(12) United States Patent
Hagl

(10) Patent No.: US 8,869,596 B2
(45) Date of Patent: Oct. 28, 2014

(54) SENSOR DEVICE

(76) Inventor: Peter Hagl, Vienna (AT)

( * ) Notice: Subject to any disclaimer, the term of this patent is extended or adjusted under 35 U.S.C. 154(b) by 221 days.

(21) Appl. No.: 13/505,134

(22) PCT Filed: Oct. 29, 2010

(86) PCT No.: PCT/AT2010/000412
§ 371 (c)(1),
(2), (4) Date: Jun. 6, 2012

(87) PCT Pub. No.: WO2011/050382
PCT Pub. Date: May 5, 2011

(65) Prior Publication Data
US 2012/0234078 A1 Sep. 20, 2012

(30) Foreign Application Priority Data

Oct. 30, 2009 (AT) ................................ A 1723/2009
Dec. 30, 2009 (AT) ................................ A 2055/2009

(51) Int. Cl.
*G01N 25/56* (2006.01)
*G01N 27/22* (2006.01)
*A61B 5/00* (2006.01)

(52) U.S. Cl.
CPC ......... *G01N 27/223* (2013.01); *A61B 2562/029* (2013.01); *A61B 5/441* (2013.01)
USPC ........................................ 73/29.05; 73/29.02

(58) Field of Classification Search
CPC ........ G01N 25/56; G01N 25/58; G01N 25/70
See application file for complete search history.

(56) References Cited

U.S. PATENT DOCUMENTS

| 2,666,897 | A | 1/1954 | Collins |
| 4,311,151 | A | 1/1982 | Hagihara |
| 6,966,877 | B2 | 11/2005 | Lahtinen |
| 2002/0137992 | A1 | 9/2002 | Lahtinen |
| 2006/0150714 | A1 | 7/2006 | Imhof |
| 2008/0125631 | A1 | 5/2008 | Imhof |
| 2008/0274511 | A1* | 11/2008 | Tan et al. ..................... 435/91.2 |

FOREIGN PATENT DOCUMENTS

| DE | 43 19 603 A1 | 12/1993 |
| DE | 100419921 A1 | 3/2002 |
| DE | 102008016157 A1 | 10/2009 |

(Continued)

OTHER PUBLICATIONS

Valentin, et al., "A Novel Transepidermal Water Loss Sensor", IEEE Sensors Journal, Aug. 2006, pp. 1022-1026, vol. 6, No. 4, ISSN : 1530-437X, URL: http://www.libsou.com/pdf/01661588.pdf.

(Continued)

*Primary Examiner* — Paul West
(74) *Attorney, Agent, or Firm* — Laurence A. Greenberg; Werner H. Stemer; Ralph E. Locher

(57) ABSTRACT

A sensor device determines an amount of liquid contained or stored in an object to be tested. The sensor device contains at least one heating element and at least one humidity sensor. When operated, the sensor device defines at least one volume which can be sealed off by placing the device on the surface of the object to be tested. The heating element is configured to heat at least part of a surface of the object delimiting the volume, the humidity sensor measuring the humidity in the interior of the volume.

12 Claims, 5 Drawing Sheets

(56) References Cited

FOREIGN PATENT DOCUMENTS

| | | |
|---|---|---|
| EP | 0 155 115 A2 | 9/1985 |
| EP | 0 376 584 A2 | 7/1990 |
| FR | 2 400 879 A1 | 3/1979 |
| GB | 2 452 258 A | 3/2009 |
| JP | 2008215873 A | 9/2008 |
| WO | 01/35816 A1 | 5/2001 |
| WO | 2004/034045 A1 | 4/2004 |
| WO | 2004/105602 A1 | 12/2004 |

OTHER PUBLICATIONS

Courbat, et al., "Ultra-low power metal-oxide gas sensor on plastic foil", Proceedings of the Transducers, Jun. 2009, pp. 584-587, vol. 1, Denver, CO, USA, URL: http://infoscience.epfl.ch/record/142322/files/Ultra-low%20power%20metal%20oxide%20gas%20sensor%20on%plastic%20foil%20(2).pdf.

Muendlein, et al., "Transepidermal water loss (TEWL) measurements with two novel sensors based on different sensing principles", URL: http://publik.tuwien.ac.at/files/pub-et_11355.pdf.

* cited by examiner

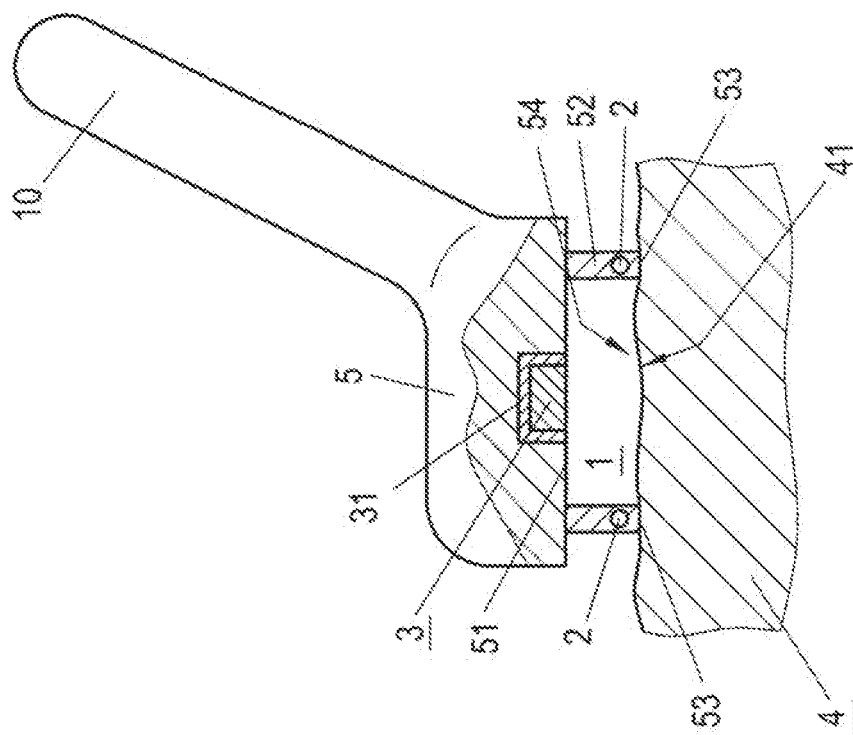
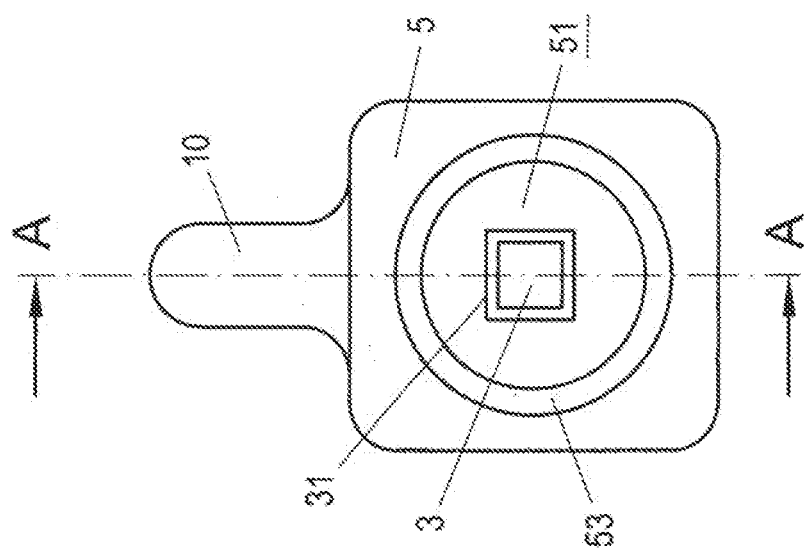

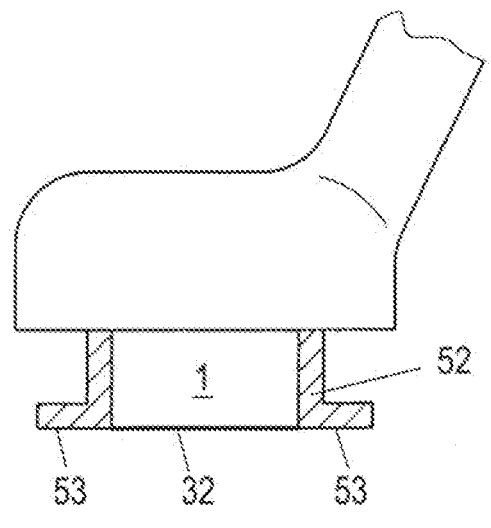
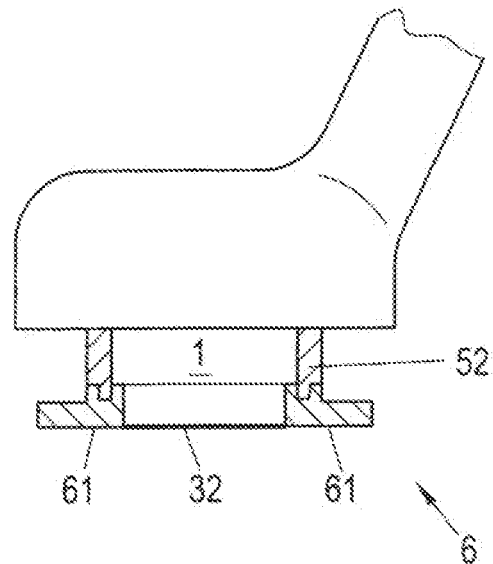
FIG. 7A          FIG. 7B
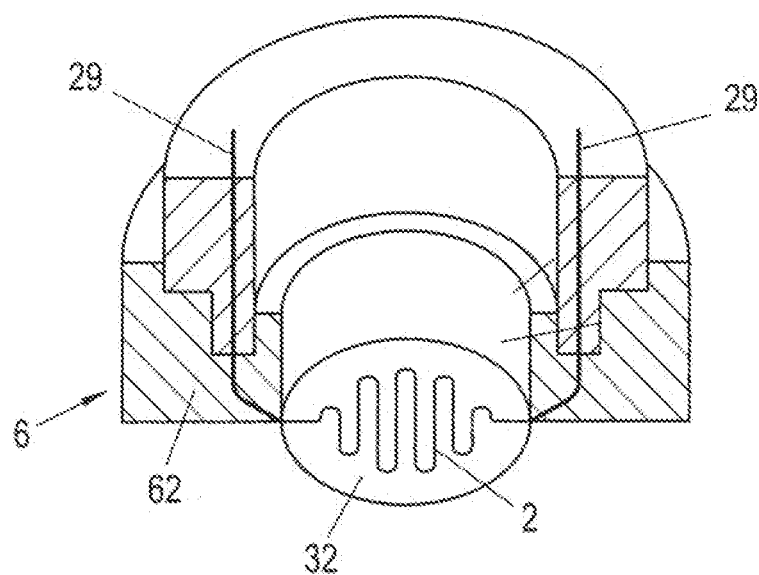
FIG. 8

SENSOR DEVICE

BACKGROUND OF THE INVENTION

Field of the Invention

The invention relates to a sensor device for determining the quantity of liquid or liquid content store in an object. The invention furthermore relates to a cap. Furthermore, the invention relates to a method for determining the quantity of liquid or liquid content stored in an object.

Hereinafter, stored humidity or moisture is considered to be the entire humidity situated in an object or in part of an object or the entire water content situated in an object or in part of an object. Water or humidity can be present in an object, as is explained below, in bound or unbound form.

Reference is made to bound humidity if it is included in or enclosed by the object. Bound humidity can, for instance, be included for example in fat or be incorporated or bound therein. However, this humidity can also be bound in cells, fibers or tissue or be included in a vapor-tight/water-tight manner. Furthermore, it is also possible for the humidity or water to be present in chemically bound fashion, for example in the form of water of crystallization.

In the case of tissues, bound humidities or water proportions are not available for liquid transport and do not evaporate or evaporate only very slowly, more particularly when the water in the substance surrounding it, for example fat, is bound to the substance by chemical or physical binding.

Humidities or water proportions which are unbound are able to evaporate and require for this purpose, depending on the type of surface constitution and temperature, air pressure and air movements at the surface of the object, a time period in order to evaporate.

BRIEF SUMMARY OF THE INVENTION

The present invention addresses the problem of providing an arrangement or device by means of which the quantity of humidity stored in an object or the humidity content thereof can be determined.

The invention solves this problem by means of the characterizing features of patent claims.

Advantageous developments of the invention are specified in the dependent claims.

The invention provides a sensor device for determining the quantity of liquid contained or stored in an object to be tested, wherein the sensor device comprises at least one heating element and at least one moisture sensor.

Furthermore, it is provided that the sensor device, during operation, forms at least one volume which can be closed off, more particularly by bearing against the surface of the object to be tested, wherein the heating element is designed for heating at least part of the surface of the object delimiting the volume, and wherein the moisture sensor measures the humidity in the interior of the volume.

This makes it possible for the humidity content stored in an object to be determined in a simple and efficient manner. By means of a calibration method, on the basis of a multiplicity of measured humidity values, e.g. based on the values of the electrical capacitance or of the electrical resistance of the humidity sensor, it is possible to determine the absolute air humidity with high accuracy. If the temperature is additionally measured as well, it is also possible to determine the relative air humidity. The accuracy of the measurement of the absolute air humidity can be increased. A further calibration can also be effected with respect to the surrounding pressure.

One preferred embodiment provides for the volume to be delimited by the sensor device, which toward one side has an opening that can be covered by the object to be tested. Furthermore, it can be provided that the sensor device comprises a housing, which delimits the volume and the opening.

This makes it possible to measure the humidity of objects in the case of relatively great air movements, which makes the sensor usable more particularly for measurements outdoors.

Furthermore, it can be provided that the housing is embodied in such a way that the volume is formed with a maximum thickness of less than 5 mm, more particularly less than 1 mm, measured normal to the opening or to the surface of the object closing the opening.

Alternatively, it can be provided that the ratio of the thickness of the volume, more particularly of the height of the projection, to the diameter or the maximum extent of the opening is 1:1 to 1:100, more particularly 1:2 to 1:20.

This enables an eddy-free measurement of the evaporating humidity and prevents convection and mixing of the vapor or emanation emerging from the object.

One preferred aspect of the invention provides for the housing to have a, preferably planar, base surface and a self-contained circumferential and/or ring-shaped projection arranged on the base surface, wherein the base surface and the projection delimit the volume and the projection delimits the opening.

This enables a particularly simple construction of a sensor device and the formation of a volume readily adaptable to objects. This furthermore ensures an air-tight seal between the object and the opening of the volume.

Moreover, it can be provided that the projection has a projection height of 1 mm to 5 mm, relative to the base surface, and the end surface of the projection facing away from the base surface forms a bearing surface for the object, wherein the end surface is, as appropriate, widened or extended toward the outside.

This enables particularly stable and air-tight bearing of the object against the sensor device.

A further preferred embodiment of the invention provides for the heating element to be arranged in the, preferably ring-shaped, projection or to form the projection.

This enables the object to be heated particularly rapidly and efficiently.

A further advantageous aspect of the invention provides for the heating element to have at least one heating wire, more particularly extending circumferentially in the ring-shaped projection, which at least one heating wire, upon abutment against the object, can be brought into thermally, more particularly directly, conductive contact with the surface of the object or runs directly on the surface of the projection.

This increases the thermal efficiency of the heating element.

It can be provided that the heating element is formed by radiation sources, more particularly LEDs, arranged on the housing and/or on the projection, more particularly on the base surface of the housing, and/or in that the heating element are arranged on a wall of the base surface or of the housing that delimits the volume.

This enables the heating of the object to be carried out more rapidly. The efficiency of the heating is additionally increased.

Furthermore, it can be provided that the ring-shaped projection is embodied in annular fashion or in the form of a circumferential rectangular ring.

As a result, an advantageous volume is formed using simple structural means.

A preferred configuration of the invention provides for at least the moisture-sensitive part of the moisture sensor to be arranged within the volume or to border the latter, and the air situated in the volume is in contact with this part, more particularly via a channel.

This enables a particularly stable arrangement of the humidity sensor and yields very precise measurements, since the heated emanation or vapor collects in the region of the humidity sensor.

It can be provided that the moisture sensor is arranged in a depression formed in the base surface and preferably terminates flush with the base surface.

A particularly simple structural measure for the arrangement of the humidity sensor is provided as a result.

A further preferred aspect of the invention provides for the moisture sensor, more particularly only its moisture-sensitive part of the surface or its part in contact with the volume, to be covered or surrounded with a water-repellent and/or vapor-permeable film, more particularly composed of Teflon.

This measure protects the humidity sensor against contaminants.

Furthermore, it can be provided that a water-vapor-permeable and/or dirt-repellent protective film is provided between the moisture sensor and the object bearing there, this protective film preventing contamination of the sensor.

The humidity sensor and those parts of the sensor arrangement which border the volume are thereby protected against contamination.

Furthermore, it can be provided that the protective film covers the opening, and/or in that the heating element is realized, as appropriate, as a heating wire arranged on the protective film, more particularly running in meandering fashion.

As a result, a particularly simple and effective arrangement of the protective film is provided. Furthermore, an effective and direct configuration of a heating element is described by the provision of a meandering heating element. In this case, the energy is introduced directly at the surface, as a result of which the object is heated particularly efficiently.

One development of the invention provides for the dirt-repellent protective film to be embodied, more particularly as a screening film, with opening sizes in the range of 10 μm to 1 mm, more particularly of 50 μm to 100 μm, and is formed more particularly by steel fabric, sintering filter, Teflon or a membrane filter.

Particularly robust and dirt-repellent types of protective films are provided as a result.

Furthermore, it can be provided that the dirt-repellent protective film is tensioned tautly. This prevents the contamination of the protective film.

A further preferred aspect of the invention provides for the volume, upon abutment of the object, to be closed off by the closing of the opening in a vapor-tight manner, preferably in an air-tight manner.

This enables complete capture of the vapor released by the object and a very accurate measurement of the humidity situated in the object.

The invention can be developed by at least one further heating element arranged in such a way that it heats the moisture sensor.

This improves the reproducibility of the measurement results, since the sensor can be brought to a defined initial state by complete evaporation of the moisture water situated in the sensor.

Furthermore, it can be provided that the further heating element surrounds the moisture sensor, more particularly is embodied as a heating wire that surrounds the moisture sensor, more particularly is wound around the latter.

A particularly effective and energy-saving embodiment of a sensor device is provided as a result.

Preferably, it can be provided that a multiplicity of moisture sensors are provided which are arranged in grid-type fashion.

As a result, a multiplicity of humidity measurements of an object can be carried out simultaneously, wherein each of the measurements measures a delimited surface area of the object.

Preferably, it can be provided that the volume is subdivided by a number of subdividing webs into a multiplicity of partial volumes which in each case upon abutment of the object are in contact with the latter and which are each assigned a moisture sensor which measures the humidity in the respective partial volume.

As a result, an effective separation of the quantities of moisture evaporated from the individual surface areas and mixings of the quantities of moisture evaporated from different surface areas are avoided.

In particular, it can be provided that a number of partial volumes are closed off in an air-tight manner at the opening upon abutment of an object and the remaining partial volumes have an air passage which is situated in the region of the humidity sensor and which, if appropriate, is linked to the surrounding air.

As a result, it is possible to measure individual surface areas at different excitation temperatures, only small quantities of energy being required for the heating of the individual surface areas of the object.

Thus, it can furthermore be provided that a housing is provided, which has an end side with a continuous opening formed therein, and that the moisture sensor closes the opening in a sealing fashion from the side situated opposite the end side, wherein the volume is formed in, before or in the region of the opening.

This configuration enables a sealed volume to be formed in a particularly simple manner.

A further aspect of the invention provides for the moisture sensor to be in contact with the heating element, more particularly by means of a thermally conductive adhesive. This improves the heat dissipation.

Moreover, it can be provided that the heating element is in contact with a thermally conductive body, more particularly consisting of aluminum or aluminum sinter. This makes it possible to form a sensor apparatus that is particularly thermally stable.

One advantageous development of the invention provides for the heating element to be embodied as a Peltier element, and in that a further volume separate from the volume is formed between the housing, the body, the heating element and the moisture sensor. This prevents a thermal short-circuit of the Peltier element and improves the efficiency. The regulation of the temperature in the volume is additionally simplified.

Furthermore, it can be provided that the housing has a channel and/or in that the body has a continuous cutout, wherein a channel is formed between this continuous cutout and the housing.

This simplifies the guidance of the electrical connections of the moisture sensor and of the heating element.

A further advantageous development of the invention provides for the body, the heating element and the moisture sensor to be pressed in the housing, wherein the housing is screwed to the body, if appropriate. A volume thus produced is particularly tight. Air cannot escape from the volume into the interior of the sensor apparatus. In particular, moisture water cannot settle in the further air volume.

Furthermore, the invention addresses the problem of providing a cap which, upon placement or coupling to the sensor device, prevents contamination of the sensor device.

The invention relates to a cap for the closing-off of the volume, more particularly of a sensor device according to the invention, preferably for placement on to the projection, comprising a ring-shaped or closed circumferential base body and a bearing surface for placing the sensor device on to an object, characterized by a vapor-permeable protective film, which is arranged in the inner region of the ring-shaped or closed circumferential base body and closes off the opening formed by the ring-shaped or closed circumferential base body, wherein the cap preferably has a wall which bears against the wall delimiting the volume and has a through-flow opening through which the air situated in the volume can be brought into contact with the moisture sensor.

This cap affords the advantage that contaminants do not penetrate as far as the sensor device; consequently, the humidity sensor and those parts of the sensor device which delimit the volume are not contaminated by the object to be tested. Moreover, the advantage in the case of application with patients is that one cap can be used for each patient, with the result that there is no transmission of germs between patients via the sensor device. Furthermore, contaminants are prevented from penetrating into the volume through the opening during evaporation, and from contaminating the humidity sensor.

One development of the invention provides for the base body to be outwardly curved in the plane of the opening formed by the ring-shaped or closed circumferential base body, as a result of which the bearing surface is outwardly extended.

This enables particularly stable and air-tight bearing of the object against the cap.

Furthermore, in one preferred development of the invention it is provided that there is arranged in the base body a heating element, more particularly in the form of a heating wire extending circumferentially in the base body, wherein the heating wire is thermally conductively coupled to the bearing surface or the heating wire runs on the bearing surface.

This enables the object to be supplied with energy and to be heated particularly efficiently.

Furthermore, it can be provided that the cap has a heating element, which is formed at or on the protective film in the form of a, more particularly imprinted, preferably meanderingly running, heating wire.

As a result, the efficiency during the heating of the object is improved, that is to say that a greater proportion of the heating energy made available is used for heating the object.

Furthermore, it can be provided that a connecting line runs in the interior of the base body of the cap and, upon being plugged on to a sensor device according to the invention, can be brought into electrical contact with an energy source situated in the sensor device.

This enables a particularly simple energy supply of, and an energy-saving embodiment of, the heating element.

Furthermore, the invention addresses the problem of providing a fast and secure method for determining the humidity incorporated in an object or for determining the humidity content of an object.

The invention provides a method for determining the quantity of liquid situated in an object. In this case, it is provided that the object is heated in a locally delimited region, the vapor released by the object in this region upon heating is collected in a volume that closes off this region, more particularly in a vapor-tight manner, the air humidity situated in the volume is measured, and this air humidity is regarded as a measurement value for the quantity of liquid stored in the object.

The method according to the invention enables the quantity of liquid situated in an object to be determined rapidly and simply.

One development of the method according to the invention provides, before and/or during the heating of the object, for the humidity of the air situated in the volume to be measured, wherein the measured humidity profile over time is regarded as an indicator of the quantity of liquid stored in the object. This development of the invention makes it possible to determine the intensity of the binding of the water situated in the object.

One particular aspect of the invention provides for the humidity to be measured at predetermined time intervals, more particularly at intervals of 1 ms to 3 s.

This enables particularly good mapping of the evaporation behavior of the quantity of humidity situated internally in the object.

Furthermore, it can be provided that the object is heated superficially by 0.01 to 5° C., more particularly 0.1° C. to 5° C., more particularly to a maximum of 43° C., preferably to 40° C. to 42° C.

This provides a gentle and efficient method for determining the moisture content of living or biological materials.

It can be provided that a predetermined quantity of heat of between $10^{-12}$ W/mm$^2$ and 0.1 W/mm$^2$, more particularly between $10^{-10}$ W/mm$^2$ and 0.1 W/mm$^2$, preferably between $10^{-10}$ W/mm$^2$ and $8 \cdot 10^{-6}$ W/mm$^2$, is applied to the object.

This enables efficient heating and prevents the destruction of the respective material to be heated.

One preferred embodiment of the method according to the invention provides for firstly the quantity of liquid stored in a reference object to be measured in accordance with a method according to the invention, and the measurement value determined by measurement of the reference object to be related to the measurement value determined by the measurement of the object, wherein, if appropriate, a multiplicity of measurements of the reference object and of the object are performed and the air humidity profiles respectively determined are subsequently determined and compared with one another and assessed, wherein the same temperature or the same quantity of heat is applied in particular to the reference object and the object in the course of heating.

This development of the method according to the invention enables an efficient calibration on the basis of reference objects.

Furthermore, it can be provided that firstly, without heating, the liquid evaporating from the object or the skin is determined and this liquid proportion is determined and assessed as unbound liquid proportion, subsequently the temperature is increased or heat is supplied, as a result of which the release of water from the object or skin increases, and the additional quantity of liquid released by the object during the heating thereof is determined and this liquid proportion is determined and assessed as bound liquid proportion.

This development of the invention makes it possible to differentiate the evaporated moisture water into proportions of water originally bound in the object and unbound water.

One development of the method according to the invention provides for the reference object used to be a human or animal body part that is free of a predetermined disease, for example free of tumors, more particularly skin tumors, or rheumatism, and corresponding body parts of persons are used as object or objects, wherein in particular an increased humidity content of the object by comparison with the reference object implies an increased risk of being affected by a disease.

This development of the invention makes it possible to ascertain or determine the risk of becoming ill with a skin disease, more particularly a skin tumor, or a disease of tissue situated beneath the skin.

Moreover, it can be provided that for the purpose of checking the release of humidity from skin cream to the skin a reference measurement is carried out by determining the humidity of a human or animal body part or tissue predetermined as reference object, subsequently skin cream is applied to this body part and allowed to act on the skin for a predetermined period of time, and subsequently the body part is subjected to a second humidity measurement, wherein the release of humidity from the skin cream is determined by relating the humidity determined in the course of the reference measurement to the humidity determined in the course of the second humidity measurement.

This makes it possible to determine the qualitative and quantitative efficacy of skin creams.

It can be provided that for determining humidity in a masonry part a predetermined quantity of heat is released to the masonry and the profile of the air humidity over a predetermined time period, more particularly from 2 to 5 minutes, is measured, wherein masonry proven to be dry is used as reference object.

Preferably, it is provided in this case that the volume is ventilated during the determination of the humidity of the masonry part or of the reference object, so that the humidity can escape with a predetermined rate from the volume.

This provides a method for determining the probability of formation of mold in buildings.

BRIEF DESCRIPTION OF THE SEVERAL VIEWS OF THE DRAWING

The invention is explained in greater detail on the basis of some exemplary embodiments with the aid of the Figures below, without restricting the general concept of the invention.

FIG. 1 shows a sensor device according to the invention from below.

FIG. 2 shows a cross section along the sectional line A-A illustrated in FIG. 1.

FIG. 7a shows a sensor device having outwardly bent or extended end surfaces. FIG. 7b shows a sensor device with a cap and with an outwardly bent base body.

FIG. 8 shows a cap with a heating element with leads.

DESCRIPTION OF THE INVENTION

Figure 3:
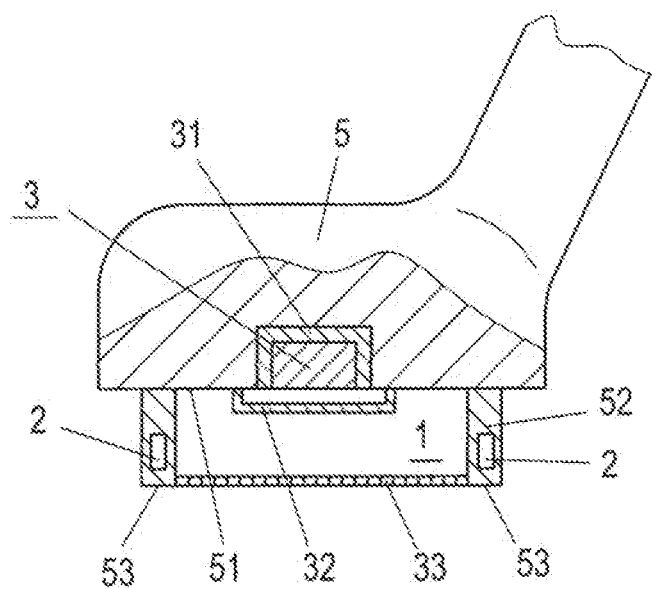
FIG. 3 shows a preferred embodiment of the head of a sensor device according to the invention with protective measures for the moisture sensor.

FIG. 1 shows a sensor device with a housing 5 comprising a handle 10. Alternatively, the sensor device can also be fixedly mounted, in which case, rather than a handle, a holding unit is then provided, with which the sensor is fixed, for example to a wall, on a framework or on the ground. With the aid of the holding device 10, the sensor device can easily be moved to a predetermined location and be brought into contact with an object 4 (FIG. 2) to be tested.

In this particular embodiment, the housing 5 comprises a planar base surface 51 having a cutout 31. A moisture sensor 3 is arranged in this cutout 31, and terminates flush with the base surface 51. Furthermore, a ring-shaped projection 52 (FIG. 2) is provided on the base surface, this projection having an end surface 53 that can be brought into contact with the object 4. In the present case, the projection 52 has an annular shape. Alternatively, it is also possible to provide a projection 52 having the form of a rectangular ring or some other circumferential self-contained shape. The projection 52 and the base surface 51 form a volume 1 (FIG. 2). In the course of a measurement, the volume 1 is delimited by the object 4 from at least one side.

The projection 52 illustrated contains an annularly circumferential heating wire as heating element 2. The heating element 2, more particularly the heating wire, can either be arranged on the surface of the projection 52 or be thermally conductively connected or coupled to the surface of the projection 52. The heating element 2 can be brought into thermally conductive contact with the object 4 by virtue of the end surface 53 bearing against the object 4. For this purpose, provision can be made, in particular, for the entire projection 52 or at least the part of the projection between the heating element 2 and the end surface 53 to consist of material having good thermal conductivity, for example composed of metal. It is advantageously provided that this thermally conductive material has a melting point that exceeds the maximum temperature achievable with the heating element 2.

Alternatively, it can be provided that the projection 52 as a whole is formed with the heating wire. In this case, the heating wire has a multiplicity of windings or turns arranged in annular or rectangular fashion. The heating wire lies directly against the base surface 51 and projects from it; a projection 52 is thus formed by the heating wire.

The term heating element 2 generally designates a device which can heat a surface of an object, at least partly, if appropriate also the volume 1 situated above this object 4. This heating can be effected by heat conduction, heat flow, thermal radiation or combinations thereof. In the simplest case, the heating element is embodied as a heating wire, for example, at or on the boundary wall of the volume 1 that can be closed off. There is the possibility of the heating of an object 4 being performed by means of thermal radiation. The arrangement of a further heating element in the region in proximity to the humidity sensor 3 also makes it possible to dry the humidity sensor 3 after its use.

In addition, by means of the heating by the heating element 2 and also by the further heating element, the temperature in the volume and also the temperature of the sensor device, more particularly of the projection 52, and of the base surface 51 can be heated to such a great extent that bacteria, viruses or other microorganisms are killed. This makes it possible to prevent microorganisms from being transmitted by the sensor device.

Alternatively, the further heating element can surround the humidity sensor 3. It is thus also possible to carry out a multiplicity of measurements with the same humidity sensor 3, without the latter attaining saturation by virtue of the humidity of a previous measurement.

In a specific humidity sensor presented further below, the moisture established when an equilibrium is present is determined upon the uptake (absorption) of the humidity by the salt and the resorption of the humidity by the salt. By heating the humidity sensor, it is possible to set the threshold of absorption/resorption in a targeted manner. Furthermore, it is also possible to provide an additional heating element 2, which does not heat, or only slightly heats, the surface of the object to be examined, but rather only or primarily heats the sensor.

It is further significant that the housing 5 forms or delimits a volume 1. The volume is closed off, more particularly in an air-tight manner, when bearing against the object 4 to be measured or to be tested. The volume 1 is delimited by a part 41 of the surface of the object. The housing 5 delimits a volume 1 which is delimited by housing parts, here the base surface 51 and the projection 52, and is open toward one side. In this case, it is not of importance—although this is entirely advantageous—for the volume 1 to be hermetically sealed, vapor-tight or air-tight. Rather, it suffices for the vapor released by the object 4 under the action of heat to collect in the volume 1. Whether small quantities of vapor in this case escape for example through openings or leaks in the abutment between the projection 52 and the object 4 is unimportant.

The projection 52 delimits an opening 54 which can be closed or is closed by the object 4 in the course of a measurement. A volume 1 is thus delimited on all sides.

The heating element 2 is arranged so that it heats at least part of that surface 41 of the object 4 which delimits the volume 1. In this case, heat emitters, more particularly infrared LEDs, can also be provided on the base surface 51 and/or on the projection 52, so as to irradiate the surface 41 and thus heat the object 4 from the surface. In principle, any type of known heating elements 2 can be provided for heating the surface 41. Furthermore, a focused or alignable radiation source can also be provided, which irradiates predetermined surface regions to be measured and thus heats and causes emanations from only a relatively small partial region of the surface, if appropriate also regions underneath.

In principle, all known types of moisture sensors, more particularly plastic sensors, silicone-based and salt-based sensors, are appropriate as the moisture sensor 3. These sensors 3 exhibit an increased conductivity and an increased electrical permittivity upon an increase in the air humidity, as a result of which the air humidity can be determined in a simple manner. In many air humidity sensors, only the capacitance changes in the event of rising or falling air humidity. Furthermore, it is possible to use sensors comprising a porous carrier material, in whose pores salt crystals are introduced. A moisture sensor 3 of this type can measure either absolute air humidity or relative air humidity. In the case of a relative air humidity determination, an additional temperature sensor is arranged in the region of the moisture sensor 3, wherein a relative air humidity value can be determined for a number of predetermined temperatures and a number of predetermined measurement values output by the moisture sensor 3, by means of calibration. What is advantageous about such a humidity sensor is that both the capacitance and the resistance change in the event of a change in humidity. This is advantageous particularly when an externally impressed capacitive coupling-in is present which changes the capacitance of the humidity sensor, since the resistance is not subjected to such a change caused by a capacitive coupling-in.

According to the invention, a sensor for determining the humidity of materials, more particularly of gases, preferably the air humidity, comprising a carrier body, to which is applied a substance that reversibly absorbs moisture from the surroundings and/or releases it to the surroundings, and at least two electrodes arranged in a manner spaced apart from one another is involved.

In this case, it is provided that the carrier body is produced from or with an open-pored porous, air-moisture-invariant, non-hygroscopic carrier material having high internal stiffness, at least the pores of the carrier material are filled or coated at least at their surfaces or walls with the substance that reversibly and reproducibly absorbs moisture water from the material or gas or air space that is brought into contact or is in contact with the carrier material of the carrier body, and/or releases it to the material or gas or air space, preferably with an inorganic salt of this type in dissolved, liquid, solid or crystalline form. The conductance and/or electrical permittivity of the said substance, more particularly of the salt, are/is reproducibly functionally dependent on the moisture of the material that is brought into contact or is in contact with the carrier material of the carrier body to which the substance is applied, more particularly the moisture of the surrounding air. With a moisture sensor 3 of this type, the air humidity can be determined rapidly, efficiently and reproducibly.

Such a moisture sensor can have the following developments. All these developments can improve the presented sensor individually and in combination.

A salt, more particularly NaCl, can be used as hygroscopic substance. It is also possible to use a solid substance containing NaCl.

The electrodes can be formed by metal incorporated into the pores of the carrier body.

The electrodes can extend into the carrier body or penetrate it, wherein the pores of the carrier body that are coated or filled with the substance are arranged in the region between the electrodes, so that a current flow and/or a charge transfer between the latter are/is made possible.

The moisture sensor 3 can be arranged at different positions in the volume 1 or in the housing 5. The important point is that the moisture sensor 3 is arranged so as to measure the humidity in the interior of the volume 1. This can be achieved firstly by means of the embodiment of the invention illustrated in FIG. 1. Secondly, the moisture sensor 3 can also be arranged in the interior of the volume 1 at a distance from the base surface 51. A further embodiment of the invention can provide for a channel (not illustrated) to issue from the volume 1, the moisture sensor 3 being arranged at the end of this channel. A multiplicity of moisture sensors 3 can also be provided. At least the moisture-sensitive part of the moisture sensor 3 is arranged in the volume 1, so that the air situated in the volume 1 can come into contact with this part.

To ensure the evaporation of a particularly large quantity of humidity, it is advantageous to provide a volume 1 having a large opening 54 toward the object 4, so that a large quantity of humidity can evaporate or vaporize and can be taken up in the volume 1. In addition, it is advantageous for the volume 1 to have only a very small height or thickness with respect to the opening 54, for instance of from 1 mm to 5 mm. The distance between the opening 54 and the base surface 51 is approximately 1 mm to 5 mm.

During operation, the sensor device is brought into contact with the object 4, as a result of which this volume 1 is delimited or closed off. Subsequently, the heating element 2 is activated and heat is transferred to the object 4.

The object is heated, as a result of which humidity emerges from the object 4 and evaporates or vaporizes into the volume 1. While without heating only the unbound humidity can be determined, which would escape from the object 4 by evaporation, heating the object 4 makes it possible to determine the extent to which an increase in temperature liberates bound humidity, which subsequently evaporates from the object 4.

In addition, there is the problem that moisture sensors 3 can yield incorrect or distorted results, or can be completely destroyed, by direct contact with water. For this purpose, it can be provided that a film 32 composed of water-repellent or water-tight and vapor-permeable substance is arranged between the moisture sensor 3 and the volume 1. Advantageously, the moisture sensor 3 is coated or surrounded directly with a nano- or micro-coating. In this case, however, it is not necessary to coat or surround the entire moisture sensor 3, but rather only those parts of the surface of the moisture sensor 3 which either are moisture-sensitive or would be destroyed by the action of water. The essential advantage of the film 32 is that it can be applied to the object 4 and, after measurement has been effected, can be removed both from the object 4 and from the sensor device. This reduces contamination, if for example the evaporations of the object 4 to be measured do not consist exclusively of water, but rather to a small extent also contain other substances such as Na+, K+, Cl−, $CO_3H$, ammonia, lactates, urea, glucose, methanol, oils and other substances which would otherwise precipitate or deposit on the humidity sensor 3.

When measuring objects 4, there is the problem of contamination of the moisture sensor 3 by the object 4 itself and/or by the surrounding air on account of the very sensitive moisture sensors 3. In this case, dust particles or hairs on the object 4 can collect in the region of the volume 1, which firstly lead to contamination of the volume 1 and secondly are hygroscopic and thus absorb water and distort the measurement. In addition, the liberated vapor can comprise substances and liquids which release their internal humidity in a time-delayed manner. For this reason, it can be provided that the boundaries of the volume 1 do not absorb, store or allow passage of any water vapor or water.

In order to remedy this problem, it can be provided that the sensor unit has a screen-type protective film 33. The openings in the screen can be angular or round. The protective film can also be realized as braiding. FIG. 3 illustrates a protective film 33 of this type and also the abovementioned film 32 that protects the moisture sensor 3 against effects of water. In the embodiment illustrated in FIG. 3, the protective film 33 is fixed to the inner side of the projection 52 and covers the opening 54.

The protective film 33 can also be realized by a protective filter. This involves steel fabric, sintered filter or membrane filter. These filters slow down the water absorption of the moisture sensor 3, which is to be taken into account in the evaluation of the measured humidity profiles. In particular, when a filter of this type is used as protective film 33, a reference measurement using the same protective film is performed in order to compensate for this delay effect of the humidity absorption.

Furthermore, the protective film 33 can alternatively be embodied with Teflon. Teflon has the advantage that it is not subject to the delay effect described above, and so passes on humidity directly to the volume 1.

Figure 6:
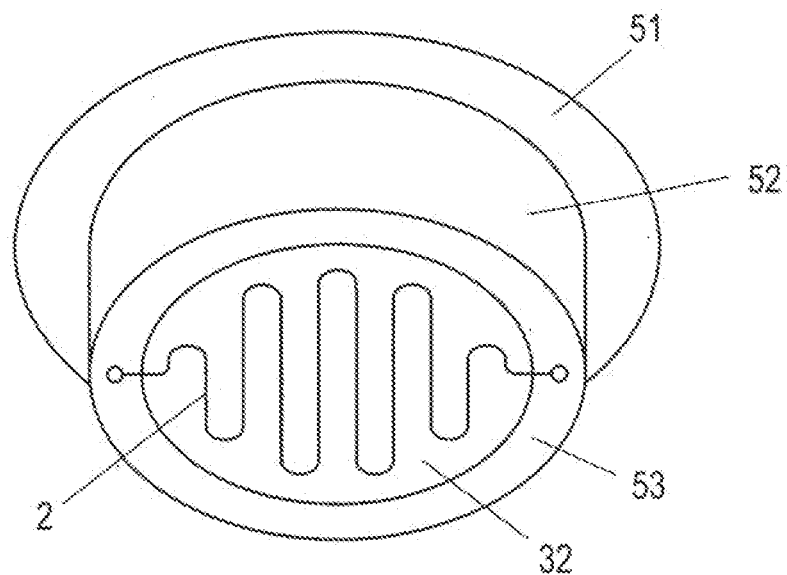
FIG. 6 shows the cap illustrated in FIG. 5, in oblique view.

Furthermore, as illustrated in FIG. 6, it can be provided that the heating element 2 is arranged on the protective film 33. In this case, the heating element 2 is preferably embodied as an electrical heating element, more particularly as a heating wire, which runs, if appropriate in meandering fashion, on the protective film 33. Particularly when heat-resistant protective films 33 are used, such an arrangement of a heating wire is advantageous since there is direct contact with the object 4 to be tested and to be heated and a very high thermal conductivity is provided. The protective film 33 and the projection 52 advantageously have a low thermal conductivity, so that only little heat is released to the sensor device, to the volume 1 or to the surroundings. The protective film 33 is vapor-permeable and heats the vapor that has emerged.

In this case, the heating wire can be printed on to the protective film 33 or woven or braided into the latter, etc. As material for the heating wire, generally all electrically conductive and thermally conductive substances are appropriate; more particularly, a metallic heating wire can be used.

Figure 5:
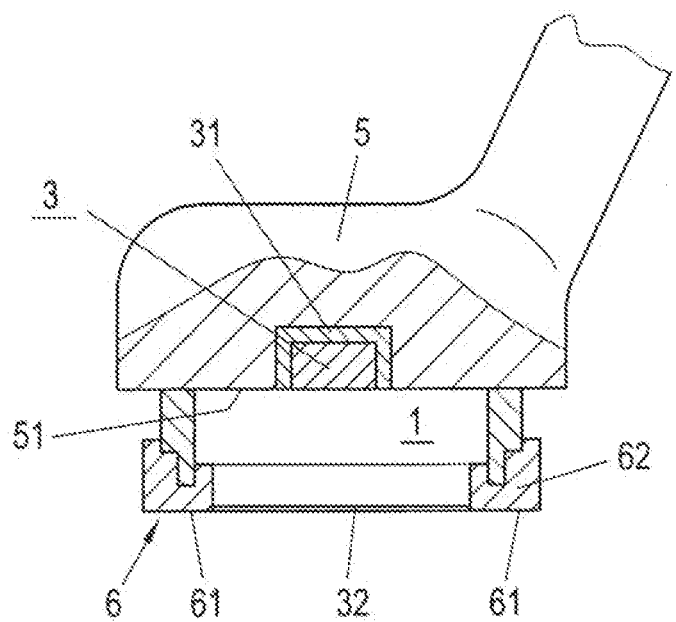
FIG. 5 shows a sensor device with cap.

FIG. 5 illustrates an alternative embodiment of a sensor device, on whose projection 52 a cap 6 is placed. Alternatively, the cap 6 can also be arranged differently; what is essential, however, is that it closes the volume 1 formed by the sensor device. The cap 6 has a bearing surface 61, against which the object 4 can be placed. In addition, there is preferably the possibility of the cap, as illustrated in FIG. 5, having a protective film 33, as already described. This affords the advantages already described; in addition, there is the advantage that contaminated protective films 33 can be exchanged together with the cap 6.

One preferred development of the invention consists in the heating element 2 being integrated into the cap 6. In this case, the heating element 2 can be arranged either in the main body 62 of the cap 6, that is to say that part of the cap 6 which is in contact with the sensor device, or else in the protective film 33. In this case, contact is made with the heating element 2 situated in the cap 6 by means of the sensor device, for example by means of electrical feed wires 29 running in the projection 52 and in the base body 62. In this case, by way of example, two supply voltage lines (not illustrated) are provided, which are led from the sensor device to the two contacts of the heating element 2. If the heating element 2 is situated in the body 62 of the cap, for example a circumferential heating wire 2 can be led in the body of the cap and be thermally coupled to the bearing surface 61 of the cap 6 facing the object 4.

Alternatively, the heating element 2 can also be supplied by means of a thermally conductive contact-connection, for example a continuous metal contact between the heating wire and the bearing surface 61, or by means of a superficial arrangement of the heating wire on the bearing surface 61.

In all of the illustrated embodiments of the invention, the heating element 2 can alternatively also be formed by a heated-up flowing heated medium and a line for guiding the medium. Either a tank for filling with the hot medium or a heat source for heating the medium is provided in this case. Such an arrangement is advantageous particularly when a predetermined temperature is not to be exceeded.

Furthermore, the heating element 2 can alternatively be realized by a vessel or a container in which are situated reagents that release heat as a result of an exothermic chemical reaction activated externally.

In all cases, the heating element 2 is arranged here in such a way that the quantity of heat generated can be released to the object 4 and can enter into it.

Both the body 62 of the cap 6 and the projection 52 can, as illustrated in FIGS. 7a and 7b, have a wide bearing surface 61 and end surface 53, respectively. This has the advantage that soft objects 4 bear better against the bearing surface 61 and the end surface 53, respectively, and are subject to a lighter pressure in the region of the opening 54. As a result, damage, destruction or injury of the object 4 can be avoided and particularly air-tight bearing of the object 4 can furthermore be achieved.

The essential advantage of the use of a cap 6 is that a separate cap 6 can be used for each object or each human or animal patient. This prevents transmission of contaminants, illnesses, fungal spores, etc. by the sensor device.

If a cap 6 is attached or applied to the sensor device, either the cap 6 or the sensor device must contain a heating element 2. If appropriate, it is also possible for a respective heating element 2 to be present both in the sensor device and in the cap 6.

One preferred embodiment of the cap 6 forms the entire volume 1, wherein just one opening is provided, through which the vapor passes to the humidity sensor.

Furthermore, the cap 6 can be developed to the effect that it is embodied as an individual injection-molded part, wherein in particular the protective film 33 is part of the injection-molded part. This has the advantage that liquid adhesives having an incorporated bound residual humidity can be avoided.

As object 4 to be measured or checked, a multiplicity of living or biological materials are also appropriate, for example wood, foodstuffs and fruit, to which humidity is harmful or the humidity content of which is regarded as a quality indicator. Human or animal or vegetable body parts or tissues are also subject to increased or reduced incorporation of humidity possibly as a result of pathological changes or changes caused by decomposition processes. The evaporation of water from the skin surface is dependent on many factors, more particularly on the temperature of the skin, the surrounding air humidity, and also on diseases, such as skin cancer, for example, which influence the incorporation of liquid under the skin.

By way of example, on account of a rheumatic disease, water is increasingly incorporated into the joints and cartilage of the hand or foot. This water is bound and cannot evaporate at normal body temperature. Upon a local increase in body temperature, part of the bound water becomes free or unbound and can evaporate from the skin. Consequently, the water emanation or vapor arising as a result of the liberation of the excessive quantity of water bound as a result of illness is superposed on the naturally emerging emanation and, consequently, after heating, a larger quantity of humidity is present than in the case of a non-rheumatic leg or a non-rheumatic hand.

Similar effects can be observed in the case of tumor diseases, in which bound humidity occurs to an increased extent in tumor tissues. This humidity can also be liberated by targeted heating and is superposed on the unbound water vapor or emanation naturally emerging at the temperature present.

In order to measure the liquid stored in the object 4, it is not necessary for the entire object to be dehydrated as a whole; this would usually not be possible without destruction of the substance of the object 4 or damage to the living tissue. Rather, it suffices to evaporate a relatively small quantity of humidity from a partial region—predetermined according to size—of the surface or surface area of the object 4 by means of heating and to measure the air humidity established in the volume 1 above the object 4. The object 4 is locally heated by the heating element 2, wherein the development of moisture is determined, if appropriate, for calibration purposes before the heating, but in any case during and/or after the heating.

Particularly meaningful results can be obtained by determining the profile of the measured humidity over time. In this case, the humidity is measured at predetermined time intervals, for instance of from 10 ms to a few seconds. After a measurement time of from a few seconds to a few minutes, a profile in the form of a curve is obtained, which can be used for determining the quantity of liquid stored in the object 4. Preferably, it is possible to perform a calibration at a predetermined temperature. An object 4 having a predetermined stored quantity of liquid is subjected to the same treatment as an object 4 to be tested. The measurement values determined for the humidity are determined separately for the object to be tested and for the reference object and are compared with one another and/or related to one another. If the reference object and the object 4 have similar quantities of liquid, they are assessed as similar.

This procedure can be performed for a multiplicity of different objects having a different humidity content and at different temperatures.

For this purpose, on the sensor device provision can be made of temperature sensors and pressure sensors that determine the temperature and the pressure, respectively, of the surrounding air and also the temperature and pressure of the air situated in the volume.

As a measure of the humidity contained in an object 4, it is possible, by way of example, to determine the air humidity attained in the volume 1 after a predetermined time or maximally attained within a period of time, which air humidity arises during an above-described treatment of the object 4 when its surface that delimits the volume 1 is subjected to a predetermined quantity of heat. If the object 4 to be measured is a body part, the latter must not be heated arbitrarily. Other biological materials, too, must not be heated above a specific temperature value. Therefore, provision is made for superficially heating the object only minimally, for instance by 0.1° C. to 1° C., which firstly prevents damage to the object to be measured, and secondly reduces the energy requirement of the heating element. Human or animal tissue can be heated to up to 43° C., preferably to 40° C. to 42° C.

Alternatively, the quantity of heat and/or the heat flow density fed to the object 4 can also be defined. The required quantity of heat and/or heat flow density depend(s) on the object, more particularly on the heat capacity thereof and the thermal conductivity thereof, and also the surrounding conditions. The heating element furthermore has an efficiency of less than 100%, that is to say that all the heat available is not fed directly to the object 4.

By way of example, a heat flow density of $10^{-12}$ W/mm$^2$ to $8 \cdot 10^{-6}$ W/mm$^2$ is used, for instance, for human or animal skin. This value is chosen so that the human or animal tissue is not destroyed and enough thermal energy is available for heating the skin. The heat flow densities mentioned are likewise readily applicable to animals.

For building materials and for wood, heat flow densities of up to a few mW/mm$^2$ can be impressed on the object 4 to be measured. In the case of paper, on account of its very thin structure, upon bearing against just one sheet, it may be sufficient to employ very low heat flow densities in the range of $10^{-10}$ W/mm$^2$-$10^{-8}$ W/mm$^2$.

One application of the invention concerns the determination of the humidity or quantity of water stored in wood. In the timber industry, the humidity content is a measure of the calorific value or heating value and hence an indicator of the quality and the achievable price. As a result of holes/gaps arising as a result of knot holes, poor storage, bark beetles or other pests, etc. or as a result of missing bark, a tree or the wood can absorb humidity and create humidity deposits and store or incorporate water internally within it. The drying of wood in drying ovens is energy-intensive and contributes to keeping the wood dry only with proper storage. Moreover, drying in a drying oven only achieves outer drying, wherein the humidity deposits situated entirely within the wood cannot be dried out or can be dried out only with considerable energetic and temporal expenditure.

Monitoring of the drying of firewood according to the invention affords the advantage that only pieces of wood or logs that have not yet been thoroughly dried have to be dried further; the remaining pieces of wood can already be processed further, which entails a considerable increase in efficiency in firewood production. This method can also be used in the monitoring of lumber.

In the application in the case of firewood, there is additionally the problem that wet or moist wood tends to burst, which firstly entails the risk of damage to the stove, and secondly also entails considerable environmental pollution. Smoke, soot and increased quantities of carbon monoxide and carbon dioxide arise as a result of the non-optimum combustion process. Particularly with regard to rising environmental requirements during the operation of stoves, prior testing of the firewood constitutes a simple method for avoiding environmentally harmful waste gases. By comparing the wood to be tested with a predetermined dry piece of wood, it is possible to determine in a simple manner whether the piece of wood is dry enough to be usable as firewood or building timber.

Moreover, knowledge about water incorporations or humidity deposits in building timber or lumber allows improved meaningfulness about the stability of load-bearing wood constituents such as beams, for example, since wood having water incorporations can deform more easily and more rapidly than dry wood without moisture incorporations. In the worst case, by measuring the humidity of installed wood, for example in a roof truss, possible material defects can be avoided and renovation measures can thus be implemented in a timely manner.

If the wood is present in the form of chips and is compressed depending on quality with approximately 25 kg/cm$^2$ for producing wood pellets, a humidity stored internally within the wood pellets can escape very poorly owing to the high pressure, as a result of which drying of the pellets is made more difficult.

The humidity stored in the pellets can thus be regarded as a risk indicator for sudden detonations in ovens. It can thus be provided that after determining the humidity, pellets having high humidity are fed to a further drying process before actual heating, in order to prevent a burst in the interior of the oven.

The production of chipboards includes two steps, in which the humidity is removed from the wood in each case in a drying boiler, wherein the finely rasped wood is subjected to a drying treatment. For the production of wood chipboards, a mixture of glue and sawn chips is used. However, the glue comprises water, which can penetrate into the wood chips again, so that further drying is necessary in order to remove the water from the chipboard. The chipboard is pressed and dried at 200° C. In this case, moister locations will dry more slowly, which can lead to a deficient quality since deformations can occur as a result of the humidity incorporations. Since veneers and cuttings, for example composed of solid wood, are applied in a wet state to the press cake, the still moist mixture of chips and glue can dry with greater difficulty, since the veneers or cuttings prevent or slow down the emergence of water. In this case, the underside and the lateral surfaces of the chipboard are easier to dry than the included humidity deposits.

During later drying without applying pressure to the wood chipboard, holes can arise if the water can evaporate. Consequently, indentations or loads can more easily lead to the initiation of cracks, which can develop into extensive cracks depending on the original distribution of the water. As time progresses, e.g. in the case of laying down the floor, the humidity incorporations internally within the press cake dry out and, where water molecules supported the structure of the boards in the wet state, now a microhole or nanohole possibly even larger holes, arise(s).

On account of the loading of the wood, e.g. by persons treading on a wooden floor, extensive cracks form which combine with other holes, as a result of which unattractive looking deformations or optically visible holes arise.

In the production of wood products it can be provided that, after the production process, the humidity of the wood product is determined according to the invention and a measurement of the humidity stored in the wood is subsequently carried out. Beforehand, the humidity is determined in the case of a reference piece of wood having the desired properties with regard to fracture stability, strength, residual water incorporation and toughness, etc. The two humidity values determined are compared with one another, wherein, upon correspondence or similar values, a quality similar to the reference product can be ascribed to the wood product to be tested. However, if the product to be tested has properties that deviate greatly from the reference product, it can either be reworked, e.g. subjected to further drying, or be rejected.

An increased internal humidity also poses a problem for tablets for medicaments, for example, since some constituents become ineffective on account of moisture water or their effectiveness is significantly reduced or else increased. All these changes in the effect of medicaments are potentially dangerous for the patient, and so the determination according to the invention of the humidity stored in the tablets can be employed in the quality control after the production of the tablets before the packaging thereof.

The consumer can also test the effectiveness of the tablet or capsule before taking it, by determining the humidity content.

The tablets are capsules, for example, more particularly hard gelatin capsules, which are intended to decompose and release their constituents for example only at the site of action in the human or animal body. In the case of increased water incorporation, however, part of the capsule does not decompose at the desired location and the active ingredients situated in the tablet are taken up at the wrong location, which can lead either to an undesired increase or to an undesired decrease in the effect of the medicament.

The internal moisture is characteristic of the effectiveness, e.g. foaming effect of soap. Dirt particles are bound better by moist soap.

Other cosmetics have the task of transporting humidity or moisture into human or animal skin. If water without additives is applied on the surface of the skin, only very little moisture penetrates into healthy skin. Therefore, creams contain additives which enclose the moisture, e.g. fatty substances from Australian sheep, etc. With the aid of these substances, the water situated in the cream can penetrate into human or animal skin. The aim is to moisturize dry brittle skin and make it appear young and dynamically fresh again.

There are two starting points for measuring the humidity stored in the cream. Firstly, the humidity evaporating from the cream can be determined and used as an indicator of the effect of the cream. However, this method is suitable only to a limited extent on account of the limited absorbency of water by the human or animal skin as just mentioned.

Alternatively, preferably the procedure adopted can be such that firstly the humidity of a body part to which cream is to be applied is measured without prior treatment. A reference humidity value is determined in the process. This can be performed by a method as already described. Subsequently, the cream is applied to the relevant body part and subsequently allowed to act. After the time of action, that part of the cream which has not yet been absorbed into the skin is wiped away from the skin.

Alternatively, the cream can be rubbed in further. This process can be repeated as desired until all of the cream has been absorbed into the skin.

Subsequently, the humidity of this body part in the same area of skin is determined again and the difference with respect to the reference measurement is determined. In this case, the ratio of the two measurement values or else the difference between the two measurement values can be determined. The two measurement values can thus be related to one another. This relation is a measure of the extent to which the humidity of the cream has been absorbed into the body part, and hence a quality indicator for the cream.

In the case of solid foodstuffs, high levels of water incorporation which go beyond the extent attained during conventional production are typically an indicator of a partly artificial manner of production. In this case, water is added to the foodstuff, which predominantly serves the purpose of increasing the price. Such methods are known for many foodstuffs, more particularly also for cheese and vegetables. The method according to the invention makes it possible to measure the stored humidities of foodstuffs to be examined and the humidities of foodstuffs having a known conventional manner of production. The values are subsequently compared with one another, wherein a deviation of the stored humidity indicates a different production method.

A popular method in the food industry is to produce foodstuffs artificially by using chemical substances, more particularly using cost-effective biological substances. Thus, artificial cheese, artificial ham, etc. are produced which differ from the natural equivalent primarily in that the incorporated humidity is significantly increased.

The type of production of foodstuffs can thus be distinguished by the method according to the invention.

During storage and transport, increased humidity provides for reduced shelf life and increased formation of mold. The quality of tobacco, coffee or spices decreases greatly with the occurrence of internal humidity. In the case of these types of product, too, quality differences can be ascertained by performing comparative measurements. In this case, a known product or reference product of identical type, in the case of which the type of production is known and storage takes place according to predetermined conditions, is compared with a product to be examined. In this case, the humidity stored in the product is respectively determined and the two humidity values determined are compared, wherein different humidity values indicate different production methods or storage. Moreover, in the case of typically dry products such as, for example, bread, cookies, potato chips, etc., if an increased humidity relative to the respective reference product is measured, storage deficiencies are deduced.

In the construction industry, the internal humidity is characteristic of the permeability of thermal insulation or the strength of materials such as, for example, bitumen, asphalt, hardened concrete, roadway surfacings. The internal air humidity is crucial when processing the material, since later drying can lead to internal bubbles or pores, etc. at those locations at which an increased internal humidity is present and the latter can dry very poorly or can no longer dry after installation. As a result, the humidity remains after the processing of the material in the masonry, building, etc., and can no longer escape, or can escape only very slowly, from it.

A humidity measurement after the installation of the material can detect humidity incorporations and represent a risk indicator for damage to constructions, more particularly roadways or insulating elements.

Moreover, the probability of mold formation is increased in the case of in constructions in which water is included. Residential areas are hugely threatened by mold infestation at humidities of above 70% to 80% relative humidity.

In order to determine humidity, a constant quantity of heat is released to the masonry and the profile of the air humidity over a predetermined time period, more particularly of 2 to 5 minutes, is measured, wherein masonry that is proven to be dry is used as a reference object. During the determination of the humidity of the masonry part or of the reference object, the volume 1 is ventilated, so that the humidity can escape from the volume 1 at a predetermined rate.

Usually, a rise up to a maximum humidity is manifested in the time profile of the humidity in the case of dry or superficially moistened masonry. After the entire quantity of water has evaporated from the masonry, the humidity decreases on account of the ventilation of the volume and attains approximately the level of the surrounding humidity after the end of the measurement.

During the measurement of masonry that has absorbed moisture into itself from the ground, there is the effect that, as a result of the local drying out of the masonry part to be tested, humidity is subsequently drawn from the masonry and the masonry never fully dries out. The humidity profile of the absorbed humidity is therefore characterized by a rise to an approximately uniform level or a subsequent fall to a level significantly increased by comparison with the surrounding air humidity.

In the paper industry, compliance with predetermined moisture limits is essential when conveying the paper via rollers, in order that no tears arise in the conveyed paper. The paper quality depends, inter alia, on the humidity stored in the paper, since paper is an ideal nutrient medium for mold or spores, etc. If paper is stacked or rolled up, for example in the case of banknotes or books or rolls of paper in the printing industry, the formation of mold is intensified since stacking prevents the evaporation of water from the paper.

By comparison with a reference paper sheet, it is possible to determine whether the water incorporations situated in the paper to be tested are greatly increased. The paper produced can in this case be fed for further drying or be rejected.

The invention can furthermore be used for determining the risk of a person becoming ill from a disease.

The measurement of an increased bound humidity within a human or animal tissue indicates an increased risk of the relevant person or the relevant animal becoming ill from a disease such as, for example, tumors, rheumatism, cancer.

Moreover, this risk estimation can be improved by measuring the stored quantity of water or quantity of liquid at different locations in the body. It is therefore possible to determine characteristic patterns of the water incorporations, which can be compared with reference values in order to determine the risk of becoming ill from the relevant disease. Furthermore, the measurement can also be carried out on removed tissue. This measurement can be obtained particularly advantageously by means of the device according to the invention.

The procedure described can therefore also be used for detecting diseases such as rheumatism or tumors in the skin. Heating to up to 43° C., more particularly to 40° C. to 42° C., is performed in this case. The water vapor or the humidity can escape from the skin at various locations, for example intercellularly, i.e. in the tissue between the cells, transcellularly, i.e. through the cells. Furthermore, the water vapor can also emerge transglandularly, i.e. through glands, and transfolicularly, i.e. along the hair cells.

Figures 4A, 4B, 4C:
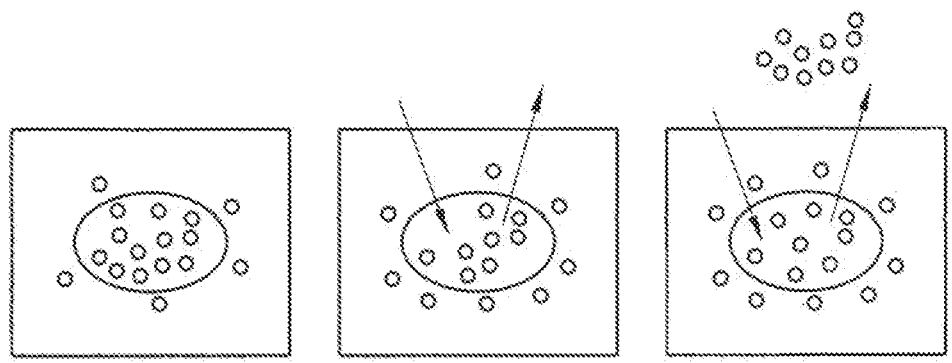
FIGS. 4a, b, c show the evaporation behavior of tissue upon supply of heat.

On account of a rheumatic disease, by way of example, water is increasingly incorporated into the joints and cartilage of the hand and/or foot (FIG. 4*a*). This water does not evaporate without thermal excitation, since it is bound water, i.e. is bound in the cells of the tissue or between the cells of the tissue.

This bound water is partly activated by introduction of heat, that is to say the bound water becomes unbound water and evaporates (FIGS. 4b, c). The quantity of evaporated liquid depends on a plurality of factors, for example the quantity of heat introduced.

On account of a tumor disease, too, for example of the skin, water is increasingly bound on the part of the tumor and is not able to evaporate without the action of temperature. The water becomes unbound and evaporates as a result of targeted introduction of heat.

For any disease that forms water incorporations under the skin or in tissue, it is possible to create a risk indicator that indicates how probable this disease is. Barrier disturbances of the human or animal skin also have a dependence on the heating, but this has a characteristic gradient or a curve profile.

In order to avoid disturbances as a result of various environmental influences as much as possible, the patient's skin can be cleaned prior to the measurement and be freed of sweat and water.

In order to determine the position of liquid incorporations in objects, more particularly in the tissue beneath the skin itself, it is possible to use an above-described device comprising a multiplicity of humidity sensors 3 arranged alongside one another. Advantageously, this sensor has a multiplicity of partial volumes which are each assigned a humidity sensor 3 that measures the humidity in the interior of the partial volume. Advantageously, the humidity sensor 3 is arranged in the interior of the respective partial volume.

Alternatively, the humidity-sensitive layer of the humidity sensor 3 can also be situated in the respective partial volume or border the latter. The humidity sensor 3 can be arranged in a cutout in a region of the base surface 51 which borders the respective partial volume. The individual partial volumes are separated from one another by subdividing webs. The partial volumes, advantageously also the subdividing webs, are in contact with the object 4 in each case when an object 4 bears against the opening 54.

A sensor device comprising a plurality of humidity sensors 3 allows the mapping of the humidity of the tissue situated under the skin onto the respective skin locations. In this case, a separate partial volume can be provided for each area of skin to be mapped. Advantageously, the moisture sensors 3 and also the partial volumes are in this case arranged in grid-type fashion. Advantageously, the partial volumes are of the same size and have the same shape and the same spatial content.

Alternatively, it is also possible to utilize the effect that the water vapor rises in laminar fashion perpendicularly up to 1.5 mm. This occurs, for instance, when half the diameter of the partial volume is greater than its height. In this case, lateral convection of the water vapor or emanation in the volume does not occur, and, consequently, nor does any mixing of the emanation above the individual skin regions.

Consequently, the emanations from the individual areas of skin can be measured or determined independently of one another. Such an arrangement makes it possible to avoid a subdivision of the volume into a multiplicity of partial volumes. Nevertheless, different areas of skin can be measured simultaneously, as a result of which images of the skin can be created.

If appropriate, an image of a body part can be created in which the respective areas of skin are colored with colors that are respectively assigned to the humidity determined for the area of skin. In this case, if appropriate, gray-scale images can also be used. The individual humidity sensors 3 are advantageously arranged in grid-type fashion.

As a result of the alteration of the temperature of the humidity sensor 3, for example as a result of heating by means of the further heating element, it is possible to set the absorption or resorption of moisture water. Resorption denotes the release of water vapor or water molecules from the humidity sensor 3, and absorption denotes the opposite process of taking up water molecules into the sensors. The air humidity is determined by the measurement of the conductance or capacitance of the humidity sensor 3. The conductance and the capacitance of the moisture-sensitive layer of the humidity sensor 3 are greatly dependent on the absorbed moisture water situated in this layer, as a result of which the air humidity in the surroundings of the humidity sensor 3 can be deduced by the measurement of the capacitance and/or conductance.

Alternatively, the current used for the measurement of the capacitance and/or resistance of the humidity sensor 3 can also be used for heating the humidity sensor.

An energy-saving alternative consists in a number of partial volumes being closed off in an air-tight manner and the remaining partial volumes having an air passage—situated in the region of the humidity sensor 3—to the surrounding air, for example via channels running in the sensor device. As a result of the air passage, a cooler temperature is attained in the partial volumes since the heat released by body or object can escape and cooler surrounding air penetrates into the partial volume. This temperature difference brings about a different evaporation behavior that allows conclusions to be drawn about the internal humidity. One essential advantage of this arrangement is that, when measuring living tissue, the internal evolution of heat in the tissue can be utilized for heating the partial volumes. In this case, the temperature established can be regulated by means of the insulation of the individual partial volumes that exists for lack of ventilation.

The volumes or the partial volumes are preferably 1 mm high, and have an area of 1 $mm^2$ to 200 $mm^2$. In the field of determining humidity of masonry, sometimes also larger areas of up to 100 $cm^2$ can be used.

If the invention is used for medical purposes, the surrounding temperature or object temperature and also the surrounding air humidity are preferably measured. This can be effected in particular by measuring devices arranged on the sensor device. If necessary, the surrounding pressure can also be determined, since the living organism, in contrast to inanimate objects, has a control loop and releases more or less air humidity into the surroundings depending on the surrounding conditions.

An example of temperature regulation of a living organism is perspiration. Upon comparing persons to be examined or tissue to be examined with healthy reference persons or healthy reference tissue, it is possible to compensate for the described surrounding factors of temperature, surrounding humidity and surrounding pressure. The difference between a healthy person and an ill examined person, after the compensation of the surrounding factors, consists merely in the liberated liquid or humidity that additionally emerges from the diseased tissue, which can be determined in a targeted manner and used as a risk indicator for the presence of a disease.

A pathological change in the skin leads to an incorporation and binding of water to the diseased cells, for example tumor cells in the case of cancer diseases, or cartilage, joint incorporations in the case of rheumatism. Without the targeted heating, these humidity constituents would not be available for transport.

By way of example, the humidity or quantitative liquid determined by the measurement of the hand cartilage or hand joints or the foot cartilage or foot joints can be used as a risk indicator for rheumatism.

In order to preclude perspiration for a patient from the outset, surrounding temperatures of less than 20° C. can be set. Taking account of this procedure or preparing the skin by wiping the examined location or carrying out the measurement rapidly is expedient.

Very generally, bound and unbound humidity can be determined separately from one another. In this case, the humidity evaporating from the object or skin is determined firstly without the action of a heating element. Next, the temperature is increased continuously or heat is supplied continuously. The release of water from the object or skin increases as a result. The additional quantity of liquid released by the object during its heating originates from originally bound water which has overcome its binding as a result of the action of heat and is freely available. Consequently, bound and unbound humidity of an object can be determined separately.

In medical applications, an additional portion, or portion that occurs relative to a reference person, of unbound water usually stems from wounds or desquamation of the skin. Additional bound water is often an indicator of a disease, for example of tumors, more particularly skin tumors, cancer or rheumatism.

Figure 9:
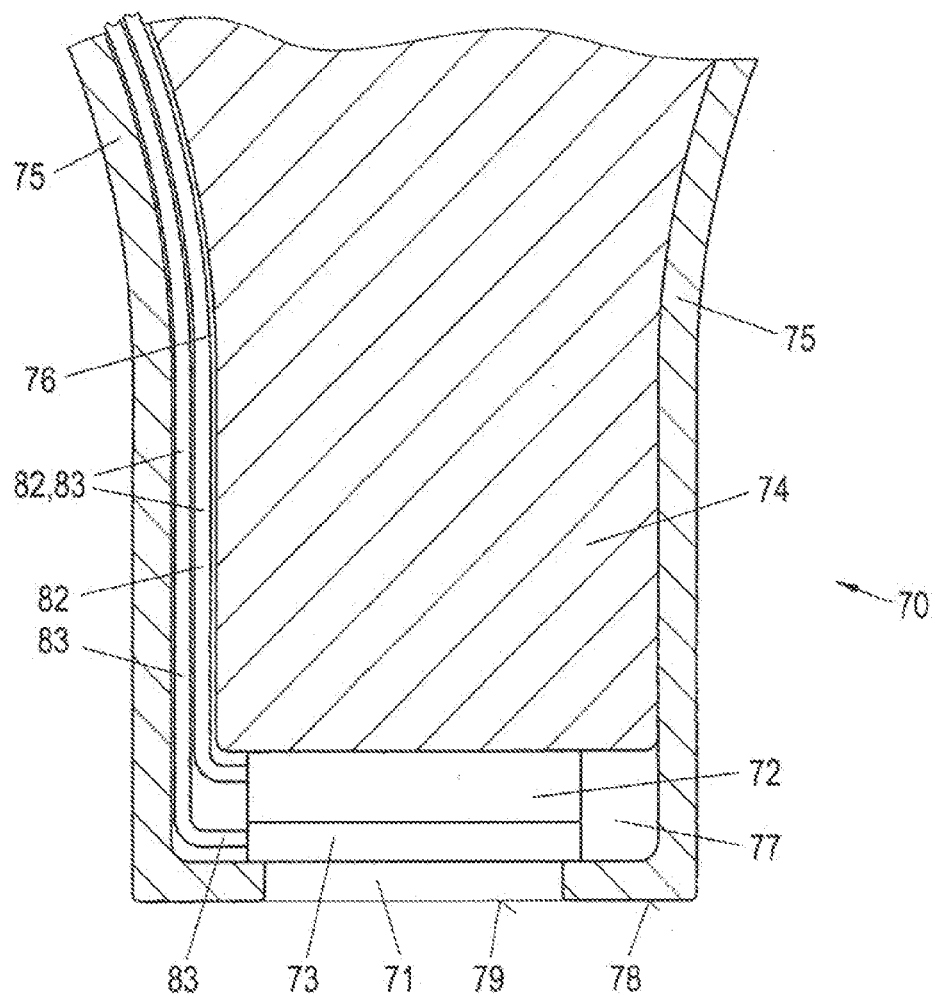
FIG. 9 shows the moisture-sensitive part of an alternative exemplary embodiment of a sensor device according to the invention which is designed for measuring the humidity stored in human and/or animal tissue.

A further exemplary embodiment, which is illustrated in FIG. 9, exhibits a specially designed measuring head 70 comprising a housing 75 having an opening 79 at its end side 78. In this particular embodiment, the housing 75 is composed of plastic.

ABS Teluran or some other plastic having a low water absorbency can also be used for producing the housing 75.

Situated behind this opening 79 is a moisture sensor 73, which closes the opening 79, so that a volume 71 is formed between the moisture sensor 73 and the opening 79 of the measuring head 70. The volume 71 has the thickness corresponding to the thickness of the housing 75 in the region of the opening 79; in the present exemplary embodiment, the thickness is approximately 1 mm. The area of the opening is approximately 4 mm$^2$ in this exemplary embodiment. The volume 71 is open from the end side 78, so that surrounding air can penetrate into the volume 71. From the opposite side, by contrast, the volume is closed by the moisture sensor 73 in an air-tight manner. The moisture sensor 73 is constructed as a humidity-sensitive, resistive and capacitive element. In this concrete embodiment, a moisture sensor 73 containing a salt is involved, as described in the introduction. It goes without saying that other moisture sensors 73 can also be used.

The connections 83 of the moisture sensor 73, which are used for the electrical measurement of the air humidity, are situated outside the volume.

A heating element 72 is arranged on that side of the moisture sensor 71 which faces away from the volume 71. In the present exemplary embodiment, a Peltier element was chosen for this purpose, but any other heating element 72 can also be chosen. The heating element 72 bears by one of its two thermally active surfaces against the moisture sensor 73 over the whole area. It is thus possible either to heat or else—should this be necessary—to cool the moisture sensor 73.

The heating element 72 has two electrical connections 82, by means of which the heating element 72, depending on the polarity, can supply heat to the moisture sensor 73 or dissipate heat from the moisture sensor 73. In this concrete embodiment, the heating element 72 is adhesively bonded to the moisture sensor 73.

Furthermore, the embodiment illustrated has a thermally conductive body 74, which consists of aluminum having a thermal conductivity of 236 W/(m·K) in the present example. Generally, other heat conductor materials such as metals, for instance, can also be used for this body 74; however, aluminum and sintered aluminum are particularly suitable. The body 74 bears areally against the moisture sensor 73. In this preferred exemplary embodiment, the body is connected to the moisture sensor 73 by means of a thermally conductive adhesive.

Furthermore, in the illustrated embodiment of the invention, the body 74 has a channel 76 for accommodating the connections 83 of the moisture sensor 73 and of the heating element 72. In this case, the diameter of the channel 76 is chosen so that the connections 83 of the moisture sensor 73 and of the heating element 72 can easily be led through. The channel 76 leads from the region of the heating element 72 and of the moisture sensor 73 bearing thereon through the body 74 to a control unit (not illustrated) located at the other end of the body 76.

Alternatively, provision can also be made for the channel 76 to be formed by a depression or notch in the body 74 and an adjoining part of the housing 75.

Measures for improving the thermal efficiency are described below on the basis of the exemplary embodiment illustrated.

The thermal conductivity of the heating element 72 and of the moisture sensor 73 is in the region of 28 W/(m·K) and approximately corresponds to the thermal conductivity of aluminum oxide (99.6% α-$Al_2O_3$). Water vapor has a thermal conductivity of 0.0248 W/(m·K). Air (21% oxygen, 78% nitrogen) has a thermal conductivity of 0.0262 W/(m·K). Precipitating water, by contrast, has a much higher thermal conductivity of 0.5562 W/(m·K).

A circumferential further volume 77, which is filled with air and is tightly separated from the volume 71, is situated laterally with respect to the heating element 73 and the moisture sensor 73, this further volume leading into the channel 76. The air in this volume 77 furthermore ensures that the thermal effect of the heating element 72 is optimized. The air space of the further volume 77 prevents the formation of an effective thermal bridge between the thermal contacts of the heating element 72 embodied as a Peltier element; the effect of the heating element 72 is optimized.

In the present exemplary embodiment, the moisture sensor 73, the heating element 72, the body 74 and the housing 75 are pressed against one another, wherein the housing 75 and the body 74 are screwed to one another in order to ensure a constant contact pressure. This pressing ensures that the volume 71 is formed particularly tightly. This can effectively avoid a situation where water having a significantly higher thermal conductivity settles in the further volume and causes a thermal short-circuit.

An alternative embodiment of the invention provides for the described pressing of the housing 75, of the body 74, of the heating element 72 and of the moisture sensor 73 to be provided instead of the adhesive bonding. This prevents a situation where otherwise the adhesive situated in the region of the opening 79 diffuses or evaporates into the volume 71 and influences the measurements.

During operation, the thermally conductive body 74 forms a heat or cold store, the internal temperature of which remains approximately the same. Influences neither of the person operating the sensor apparatus nor of that person whose skin humidity is being measured, nor of the required heating by the heating element 72 have significant effects on the temperature of the conductive body 74. The housing 75 itself has no appreciable thermal conductivity and heat capacity. Since the housing 75 touches the heating element 72 and the moisture sensor 73 only at a few points and the further volume 77 filled with air is formed between the housing 75, the heating element 72 and the moisture sensor 73, only small thermal influences occur between the housing 75 and the heating element 72 or the moisture sensor 73.

The moisture sensor 73 and the volume 71 can be kept at a constant temperature by the heating element 72 embodied as a Peltier element, as a result of which the influence of temperature on the measurement is influenced only to a small extent.

Arranged in the region of the volume 71 is a temperature sensor, by means of the measured value of which the heating element 72 is driven and the temperature is kept constant. In an alternative embodiment, a temperature regulation can also be omitted.

The housing 75 is connected to an operating device (not illustrated) having a handle. The operating device has a display and the control unit connected to the connections 82, 83 of the heating element 72 and of the moisture sensor 73. Furthermore, a trigger button for initiating the measurement is present.

The invention claimed is:

1. A sensor device for determining a quantity of liquid contained or stored in an object to be tested, the sensor device comprising:
at least one heating element;
at least one moisture sensor, the sensor device, during operation, forming at least one volume which can be closed off, by the sensor device bearing against a surface of the object to be tested, said moisture sensor measuring humidity in an interior of the volume;
said heating element configured for heating at least part of the surface of the object delimiting the volume;
a housing having an end side with a continuous opening formed therein, said moisture sensor closing said continuous opening in a sealing fashion from a side situated opposite said end side, wherein the volume is formed in a region of said continuous opening;
said moisture sensor being in contact with said heating element, and the volume having a thickness corresponding to a thickness of said housing in said region of said continuous opening;
a thermally conductive adhesive, said moisture sensor being in contact with said heating element by means of said thermally conductive adhesive; and
a thermally conductive body, said heating element being in contact with said thermally conductive body.

2. The sensor device according to claim 1, wherein the thickness of the volume amounts to 1 mm.

3. The sensor device according to claim 1, wherein:
said heating element is embodied as a Peltier element, and in that a further volume separate from the volume is formed between said housing, said thermally conductive body, said heating element and said moisture sensor; and
said moisture sensor, said heating element, said thermally conductive body are pressed in said housing and said housing is screwed to said thermally conductive body.

4. The sensor device according to claim 1, wherein said housing has a channel and said thermally conductive body has a continuous cutout, said channel is formed between said continuous cutout and said housing.

5. The sensor device according to claim 1, wherein:
said thermally conductive body, said heating element and said moisture sensor are pressed in said housing;
said housing is screwed to said thermally conductive body; and
said housing and said moisture sensor are connected to one another in the region of said continuous opening exclusively by pressing, in a manner free of adhesive, with one another in a manner sealing off the volume.

6. The sensor device according to claim 1, wherein said thermally conductive body is formed from a material selected from the group consisting of aluminum and aluminum sinter.

7. A method of measuring humidity, which comprises the steps of:
providing a sensor device containing at least one heating element, at least one moisture sensor, the sensor device, during operation, forming at least one volume which can be closed off, by bearing against a surface of an object to be tested, the moisture sensor measuring the humidity in an interior of the volume, the heating element configured for heating at least part of the surface of the object delimiting the volume, a housing having an end side with a continuous opening formed therein, the moisture sensor closing the continuous opening in a sealing fashion from a side situated opposite the end side, wherein the volume is formed in a region of the continuous opening, and the moisture sensor being in contact with the heating element, and the volume having a thickness corresponding to a thickness of the housing in the region of the continuous opening;
providing a thermally conductive adhesive, the moisture sensor being in contact with the heating element by means of the thermally conductive adhesive;
providing a thermally conductive body, the heating element being in contact with the thermally conductive body; and
using the sensor device to determine a humidity content of the object selected from the group consisting of a wood product and a product made of paper.

8. A method of measuring humidity, which comprises the steps of:
providing a sensor device containing at least one heating element, at least one moisture sensor, the sensor device, during operation, forming at least one volume which can be closed off, by bearing against a surface of an object to be tested, the moisture sensor measuring the humidity in an interior of the volume, the heating element configured for heating at least part of the surface of the object delimiting the volume, a housing having an end side with a continuous opening formed therein, the moisture sensor closing the continuous opening in a sealing fashion from a side situated opposite the end side, wherein the volume is formed in a region of the continuous opening, and the moisture sensor being in contact with the heating element, and the volume having a thickness corresponding to a thickness of the housing in the region of the continuous opening;
providing a thermally conductive adhesive, the moisture sensor being in contact with the heating element by means of the thermally conductive adhesive;
providing a thermally conductive body, the heating element being in contact with the thermally conductive body; and
using the sensor device to determine a humidity content of the object selected from the group consisting of skin of a person and skin of an animal.

9. A method of measuring humidity, which comprises the steps of:
providing a sensor device containing at least one heating element, at least one moisture sensor, the sensor device, during operation, forming at least one volume which can be closed off, by bearing against a surface of an object to be tested, the moisture sensor measuring the humidity in an interior of the volume, the heating element configured for heating at least part of the surface of the object delimiting the volume, a housing having an end side with a continuous opening formed therein, the moisture sensor closing the continuous opening in a sealing fashion from a side situated opposite the end side, wherein the volume is formed in a region of the continuous opening, and the moisture sensor being in contact with the heating element, and the volume having a thickness corresponding to a thickness of the housing in the region of the continuous opening;

providing a thermally conductive adhesive, the moisture sensor being in contact with the heating element by means of the thermally conductive adhesive;

providing a thermally conductive body, the heating element being in contact with the thermally conductive body; and using the sensor device to determine a humidity content of the object selected from the group consisting of masonry, a building, asphalt and concrete.

10. A method of measuring humidity, which comprises the steps of:

providing a sensor device containing at least one heating element, at least one moisture sensor, the sensor device, during operation, forming at least one volume which can be closed off, by bearing against a surface of an object to be tested, the moisture sensor measuring the humidity in an interior of the volume, the heating element configured for heating at least part of the surface of the object delimiting the volume, a housing having an end side with a continuous opening formed therein, the moisture sensor closing the continuous opening in a sealing fashion from a side situated opposite the end side, wherein the volume is formed in a region of the continuous opening, and the moisture sensor being in contact with the heating element, and the volume having a thickness corresponding to a thickness of the housing in the region of the continuous opening;

providing a thermally conductive adhesive, the moisture sensor being in contact with the heating element by means of the thermally conductive adhesive;

providing a thermally conductive body, the heating element being in contact with the thermally conductive body; and using the sensor device to determine a humidity content of foodstuffs.

11. A method of measuring humidity, which comprises the steps of:

providing a sensor device containing at least one heating element, at least one moisture sensor, the sensor device, during operation, forming at least one volume which can be closed off, by bearing against a surface of an object to be tested, the moisture sensor measuring the humidity in an interior of the volume, the heating element configured for heating at least part of the surface of the object delimiting the volume, a housing having an end side with a continuous opening formed therein, the moisture sensor closing the continuous opening in a sealing fashion from a side situated opposite the end side, wherein the volume is formed in a region of the continuous opening, and the moisture sensor being in contact with the heating element, and the volume having a thickness corresponding to a thickness of the housing in the region of the continuous opening;

providing a thermally conductive adhesive, the moisture sensor being in contact with the heating element by means of the thermally conductive adhesive;

providing a thermally conductive body, the heating element being in contact with the thermally conductive body; and using the sensor device to determine a humidity content of medications.

12. The method of measuring humidity according to claim 11, which further comprises measuring the humidity content of hard gelatin capsules.

* * * * *